United States Patent
Okolo et al.

(10) Patent No.: US 11,753,359 B2
(45) Date of Patent: Sep. 12, 2023

(54) ONLINE METHOD FOR PROCESSING WAX-CONTAINING CRUDE METHANOL STREAM

(71) Applicant: SABIC GLOBAL TECHNOLOGIES B.V., Bergen Op Zoom (NL)

(72) Inventors: Christian Okolo, Geleen (NL); Venkata Malleswara Rao Tadiboyina, Geleen (NL); Kuangyao Brian Peng, Sugar Land, TX (US); Mubarik Ali Bashir, Riyadh (SA)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 17/608,899

(22) PCT Filed: May 19, 2020

(86) PCT No.: PCT/IB2020/054742
§ 371 (c)(1),
(2) Date: Nov. 4, 2021

(87) PCT Pub. No.: WO2020/234772
PCT Pub. Date: Nov. 26, 2020

(65) Prior Publication Data
US 2022/0298091 A1 Sep. 22, 2022

(30) Foreign Application Priority Data

May 20, 2019 (EP) ..................................... 19175454

(51) Int. Cl.
*C07C 29/78* (2006.01)
*B01D 5/00* (2006.01)
(Continued)

(52) U.S. Cl.
CPC ............ *C07C 29/78* (2013.01); *B01D 5/0072* (2013.01); *C07C 29/1516* (2013.01); *C07C 29/86* (2013.01); *C07C 31/04* (2013.01)

(58) Field of Classification Search
CPC ..... C07C 29/78; C07C 29/86; C07C 29/1516; C07C 31/04; B01D 5/0072
See application file for complete search history.

(56) References Cited

U.S. PATENT DOCUMENTS 8,220,266 B2    7/2012  Smith

FOREIGN PATENT DOCUMENTS

| CN | 202403609 | 8/2012 |
| CN | 102865754 | 1/2013 |

(Continued)

OTHER PUBLICATIONS

CN109758821, Li Daming et al., Methanol filtering device, system and method for wax removal of methanol system, English translation 12 pages (Year: 2019).*

(Continued)

*Primary Examiner* — Yate' K Cutliff
(74) *Attorney, Agent, or Firm* — Norton Rose Fulbright US LLP

(57) ABSTRACT

Systems and methods for processing crude methanol are disclosed. A crude methanol stream, comprising methanol and paraffin wax, is produced from syngas (carbon monoxide, carbon dioxide, and hydrogen). The crude methanol stream is cooled to form a partially condensed crude methanol stream, which is further separated in a vapor-liquid separator to form a liquid stream and a gas stream. The liquid stream is further cooled in a dewaxing unit to remove paraffin wax. The dewaxing unit includes two or more cooling units arranged in parallel such that when one of the (Continued)

cooling units is offline for cleaning, the methanol system does not need to be shut down.

21 Claims, 4 Drawing Sheets

(51) Int. Cl.
   *C07C 29/151* (2006.01)
   *C07C 29/86* (2006.01)
   *C07C 31/04* (2006.01)

(56) References Cited

FOREIGN PATENT DOCUMENTS

| | | |
|---|---|---|
| CN | 102895795 | 1/2013 |
| CN | 202808648 | 3/2013 |
| CN | 202814141 | 3/2013 |
| CN | 204022708 | 12/2014 |
| CN | 104402674 | 3/2015 |
| CN | 104998427 | 10/2015 |
| CN | 105481646 | 4/2016 |
| CN | 105777491 | 7/2016 |
| CN | 105999750 | 10/2016 |
| CN | 205913793 | 2/2017 |
| CN | 106977371 | 7/2017 |
| CN | 106977371 A * | 7/2017 |
| CN | 206886988 | 1/2018 |
| CN | 109758821 | 5/2019 |
| JP | S61257934 | 11/1986 |
| WO | WO 2007/040401 | 4/2007 |
| WO | WO 2017/081602 | 5/2017 |
| WO | WO 2019/016757 | 1/2019 |

OTHER PUBLICATIONS

CN106977371, Wu, Jian-Ming, Methanol Treatment System, English translation, 9 pages (Year: 2017).*
International Search Report and Written Opinion for Application No. PCT/IB2020/054742, dated Aug. 18, 2020, 15 pages. (
Meng X.-G. and Ma S.-Q, "Generation mechanism and suppression of wax in methanol production", Xiandai Huagong/Modern Chemical Industry. (Xiandai Huagong/Modern Chemical Industry, Oct. 20, 2016, 36(10):165-167) (English Abstract).
Office Action issued in corresponding GCC Application No. 2020-39788, dated Aug. 16, 2021.

* cited by examiner

ONLINE METHOD FOR PROCESSING WAX-CONTAINING CRUDE METHANOL STREAM

CROSS REFERENCE TO RELATED APPLICATIONS

This application is a national phase under 35 U.S.C. § 371 of International Application No. PCT/IB2020/054742, filed May 19, 2020, which claims the benefit of priority to European Patent Application No. 19175454.8, filed May 20, 2019, the entire contents of each of which are hereby incorporated by reference in their entirety.

FIELD OF INVENTION

The present invention generally relates to systems and methods for producing methanol. More specifically, the present invention relates to systems and methods that use parallel cooling units for removing paraffin wax produced as a byproduct in a methanol production unit.

BACKGROUND OF THE INVENTION

Methanol is a colorless and flammable liquid that can be used in numerous chemical production processes and industry sectors. Methanol can be used as a raw material for producing formaldehyde, which is widely used in producing polymers. Methanol can also be used to produce olefins and gasoline via various catalytic processes. Methanol can also be used to produce biodiesel via transesterification reaction with glycerides. Additionally, methanol is used as a co-solvent blended in gasoline or directly as a fuel.

Currently, the most widely used process for producing methanol includes a catalytic reaction between carbon monoxide, carbon dioxide and hydrogen. In this process, by-products, including paraffin wax, are produced and mixed with the methanol. The paraffin wax is subsequently removed by coolers. During the cooling process, the solid paraffin wax can deposit in the cooler tubes, resulting in decreased heat transfer coefficient and overall cooling capacity of the cooler. As the paraffin wax deposit grows thicker and consequently the production capacity of methanol cannot be sustained, the methanol production system has to be shut down to conduct the cleaning process for the cooler, leading to loss of production days and the decreased time on stream of the whole system.

Overall, while the systems and methods of producing methanol exist, the need for improvements in this field persists in light of at least the aforementioned drawback for the methods.

BRIEF SUMMARY OF THE INVENTION

A solution to the above-mentioned problems associated with the production process for methanol using syngas (hydrogen, carbon monoxide, and carbon dioxide) has been discovered. The solution resides in a method of processing crude methanol that is produced using syngas. The method includes cooling a crude methanol stream to produce a liquid stream comprising crude methanol and paraffin wax, and further cooling the liquid stream in a dewaxing unit that includes two or more cooling units arranged in parallel with each other. This is beneficial for at least separately controlling each of the cooling units such that when one of the cooling units is off-line for cleaning, the other cooling unit can be in operation to keep the whole methanol production system on stream. Consequently, the method can prevent a total shutdown of the methanol production system caused by the need for cleaning out the wax accumulation in the cooling unit. Thus, this method can reduce or eliminate loss of production time suffered by the conventional system and method for producing methanol. Therefore, the methods of the present invention provide a technical solution to at least some of the problems associated with the conventional systems and methods for producing methanol mentioned above.

Embodiments of the invention include a method of processing crude methanol that comprises paraffin wax. The method comprises processing a crude methanol stream to produce a first liquid stream comprising primarily water, methanol, and paraffin wax, collectively. The method further comprises flowing the first liquid stream to a dewaxing unit. The dewaxing unit comprises (a) a feed inlet and (b) a first cooling unit and a second cooling unit arranged in parallel with each other. The dewaxing unit is adapted such that the dewaxing unit feed inlet is in fluid communication with the first cooling unit, or the second cooling unit, or both. The fluid communication is controlled by one or more valves between and/or in fluid communication with the dewaxing unit feed inlet and first cooling unit, and/or one or more valves between and/or in fluid communication with the dewaxing unit feed inlet and the second cooling unit. The method further comprises separating the first liquid stream, in the dewaxing unit, to form (1) a paraffin wax stream comprising primarily paraffin wax and (2) a dewaxed crude methanol stream.

Embodiments of the invention include a method of processing crude methanol that comprises paraffin wax. The method comprises processing a crude methanol stream to produce a first liquid stream comprising primarily water, methanol, and paraffin wax, collectively. The dewaxing unit comprises a dewaxing unit feed inlet. The dewaxing unit further comprises a first cooling unit and a second cooling unit arranged in parallel with each other. The dewaxing unit is adapted such that the dewaxing unit feed inlet is in fluid communication with the first cooling unit, or the second cooling unit, or both. The fluid communication is controlled by one or more valves between and/or in fluid communication with the dewaxing unit feed inlet and first cooling unit, and/or one or more valves between and/or in fluid communication with the dewaxing unit feed inlet and second cooling unit. The dewaxing unit further comprises (1) a filter feed inlet and (2) a first hydrophobic filter and a second hydrophobic filter arranged in parallel with each other. The dewaxing unit is adapted such that the filter feed inlet is in fluid communication with the first hydrophobic filter, or the second hydrophobic filter, or both. The fluid communication is controlled by one or more valves between and/or in fluid communication with the filter feed inlet and the first hydrophobic filter, and/or one or more valves between and/or in fluid communication with the filter feed inlet and the second hydrophobic filter. The method further comprises separating the first liquid stream, in the dewaxing unit, to form (1) a paraffin wax stream comprising primarily paraffin wax and (2) a dewaxed crude methanol stream.

Embodiments of the invention include a method of processing crude methanol that comprises paraffin wax. The method comprises flowing a crude methanol stream comprising paraffin wax to a heat exchanger. The method further comprises cooling the crude methanol stream, by the heat exchanger, to form a cooled crude methanol stream at a temperature in a range of 120 to 135° C. and/or that comprises a 94 to 98 vol. % vapor. The method further comprises flowing the cooled crude methanol stream to a first condenser. The method further comprises cooling the cooled crude methanol stream, in the first condenser, to form a partially condensed stream at a temperature of 72 to 80° C. and/or that comprises a 86 to 90 vol. % vapor. The method further comprises flowing the partially condensed stream to a first separator. The method further comprises separating the partially condensed stream, by the first separator, to form at least (1) a first vapor stream comprising one or more of hydrogen, carbon monoxide, carbon dioxide, methane, nitrogen, uncondensed methanol, and water; and (2) a first liquid stream comprising primarily water, methanol, and paraffin wax, collectively. The method further comprises flowing the first vapor stream to a second condenser. The method further comprises cooling the first vapor stream, in the second condenser, to form a cooled first vapor stream at a temperature of 45° C. or less. The method further comprises flowing the cooled first vapor stream to a second separator. The method further still comprises separating the cooled first vapor stream, by the second separator, to form at least (1) a second vapor stream comprising one or more of synthesis gas, nitrogen, and methane and (2) a second liquid stream comprising primarily methanol. The method further comprises flowing the first liquid stream to a dewaxing unit. The dewaxing unit comprises a dewaxing unit feed inlet. The method further comprises a first cooling unit and a second cooling unit arranged in parallel with each other. The dewaxing unit is adapted such that the dewaxing unit feed inlet is in fluid communication with the first cooling unit, or the second cooling unit, or both. The fluid communication is controlled by one or more valves between and/or in fluid communication with the dewaxing unit feed inlet and the first cooling unit, and/or one or more valves between and/or in fluid communication with the dewaxing unit feed inlet and the second cooling unit. The dewaxing unit further comprises a filter feed inlet. The dewaxing unit further comprises a first hydrophobic filter and a second hydrophobic filter arranged in parallel with each other. The dewaxing unit is adapted such that the filter feed inlet is in fluid communication with the first hydrophobic filter, or the second hydrophobic filter, or both. The fluid communication is controlled by one or more valves between and/or in fluid communication with the filter feed inlet and the first hydrophobic filter, and/or one or more valves between and/or in fluid communication the filter feed inlet and the second hydrophobic filter. The method further still comprises separating the first liquid stream, in the dewaxing unit, to form (1) a paraffin wax stream comprising primarily paraffin wax and (2) a dewaxed crude methanol stream comprising primarily methanol.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, methanol is produced via a catalytic reaction of carbon monoxide, carbon dioxide, and hydrogen. The produced crude methanol, which comprises paraffin wax as a byproduct, is then condensed in a series of cooling units to remove the wax and purify the methanol. However, due to the gradual deposition of the paraffin wax in the cooling units, the heat transfer coefficient and cooling capacity of the cooling units decreases toward a point where the production rate of dewaxed crude methanol cannot meet the production requirement. Conventionally, the whole methanol production system has to be shut down in order to clean the cooling units, resulting in loss of production time and on stream time of the production system. The present invention provides a solution to at least this problem. The solution is premised on a method of processing crude methanol that comprises cooling the crude methanol produced using syngas by two or more cooling units arranged in parallel such that when one of the cooling units is taken offline, e.g., for cleaning, the system can maintain on stream by using the other cooling unit(s) in the system. Hence, the overall production time and on stream time for the methanol production system can be improved compared to the conventional approach, which can result in increased productivity for methanol compared to the conventional method. This and other non-limiting aspects of the present invention are discussed in further detail in the following sections.

A. System for Producing Methanol

Figure 1A:
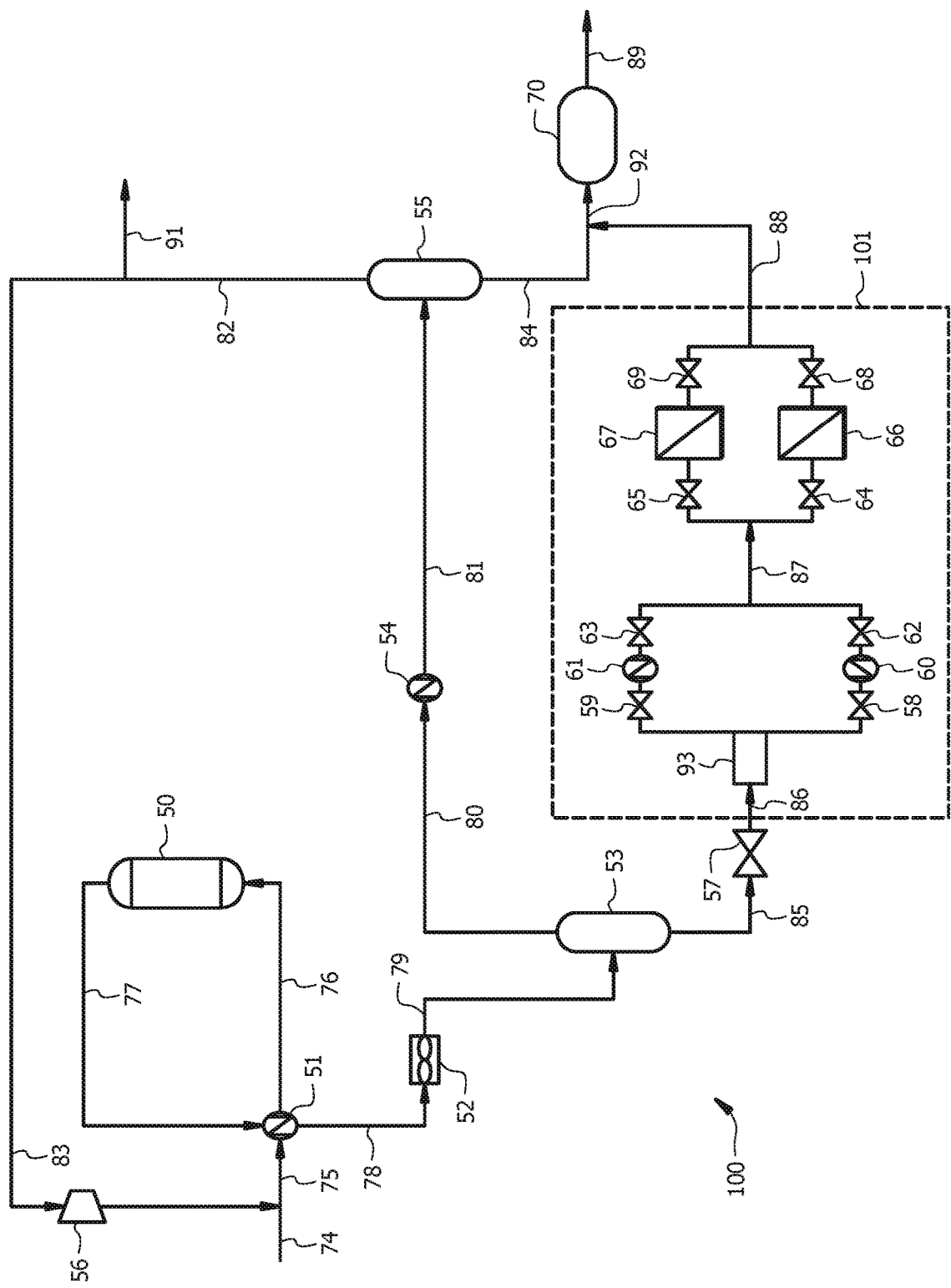
FIG. 1A shows a schematic diagram of a system for producing methanol that includes a vapor-liquid separator for separating an effluent of the methanol synthesis unit, according to embodiments of the invention.

In embodiments of the invention, the system for producing methanol includes a methanol synthesis unit, a dewaxing unit, and one or more gas-liquid separators. With reference to FIG. 1A, a schematic diagram is shown of system 100 that is capable of continuously producing methanol without system shutdowns that are caused by accumulation of paraffin wax in the dewaxing unit. According to embodiments of the invention, system 100 may include methanol synthesis unit 50 adapted to react hydrogen with carbon monoxide and carbon dioxide of heated feed stream 76 to produce product stream 77 comprising crude methanol. Crude methanol may comprise methanol; paraffin wax; water; other byproducts (e.g., ethanol); unreacted synthesis gas including carbon monoxide, carbon dioxide, hydrogen, methane, and inert gas (e.g., nitrogen); or combinations thereof. The paraffin wax may include $C_{18}$ paraffin ($C_{18}H_{38}$) to $C_{60}$ paraffin ($C_{60}H_{122}$). In embodiments of the invention, methanol synthesis unit 50 includes a catalyst comprising CuO, ZnO, $Al_2O_3$, or combinations thereof. In embodiments of the invention, heated feed stream 76 is at a temperature of 165 to 180° C. and all ranges and values there between including ranges of 165 to 166° C., 166 to 167° C., 167 to 168° C., 168 to 169° C., 169 to 170° C., 170 to 171° C., 171 to 172° C., 172 to 173° C., 173 to 174° C., 174 to 175° C., 175 to 176° C., 176 to 177° C., 177 to 178° C., 178 to 179° C., and 179 to 180° C. Product stream 77 may be at a temperature in a range of 205 to 235° C. and all ranges and values there between including ranges of 205 to 207° C., 207 to 209° C., 209 to 211° C., 211 to 213° C., 213 to 215° C., 215 to 217° C., 217 to 219° C., 219 to 221° C., 221 to 223° C., 223 to 225° C., 225 to 227° C., 227 to 229° C., 229 to 231° C., 231 to 233° C., and 233 to 235° C. Product stream 77 may be at a pressure of 80 to 110 kg/cm² and all ranges and values there between including ranges of 80 to 82 kg/cm², 82 to 84 kg/cm², 84 to 86 kg/cm², 86 to 88 kg/cm², 88 to 90 kg/cm², 90 to 92 kg/cm², 92 to 94 kg/cm², 94 to 96 kg/cm², 96 to 98 kg/cm², 98 to 100 kg/cm², 100 to 102 kg/cm², 102 to 104 kg/cm², 104 to 106 kg/cm², 106 to 108 kg/cm², and 108 to 110 kg/cm².

According to embodiments of the invention, system 100 may comprise feed effluent heat exchanger 51 configured to cool product stream 77 to produce first cooled product stream 78 and heat feed stream 75 to produce heated feed stream 76. In embodiments of the invention, an outlet of feed effluent heat exchanger 51 is in fluid communication with an inlet of cooler 52 such that first cooled product stream 78 flows from feed effluent heat exchanger 51 to cooler 52. In embodiments of the invention, cooler 52 is adapted to cool first cooled product stream 78 to produce second cooled product stream 79. Second cooled product stream 79 may be at a temperature of 72 to 80° C. and all ranges and values there between including ranges of 72 to 73° C., 73 to 74° C., 74 to 75° C., 75 to 76° C., 76 to 77° C., 77 to 78° C., 78 to 79° C., and 79 to 80° C. According embodiments of the invention, cooler 52 includes an air cooler.

According to embodiments of the invention, an outlet of cooler 52 is in fluid communication with an inlet of first vapor-liquid separator 53 such that second cooled product stream 79 flows from cooler 52 to first vapor-liquid separator 53. First vapor-liquid separator 53 may be adapted to separate second cooled product stream 79 into first vapor stream 80 and liquid crude methanol stream 85. In embodiments of the invention, first vapor-liquid separator 53 is a high pressure vapor-liquid separator. The high pressure vapor-liquid separator may be operated in a pressure range of 80 to 95 bar and all ranges and values there between including ranges of 80 to 81 bar, 81 to 82 bar, 82 to 83 bar, 83 to 84 bar, 84 to 85 bar, 85 to 86 bar, 86 to 87 bar, 87 to 88 bar, 88 to 89 bar, 89 to 90 bar, 90 to 91 bar, 91 to 92 bar, 92 to 93 bar, 93 to 94 bar, and 94 to 95 bar. First vapor stream 80 may comprise unreacted carbon monoxide, unreacted hydrogen, unreacted carbon dioxide, nitrogen, methane, and uncondensed methanol. Liquid crude methanol stream 85 may comprise methanol, water, and paraffin wax. In embodiments of the invention, liquid crude methanol stream 85 comprises about 67 to 75% of methanol from second cooled product stream 79. Liquid crude methanol stream 85 may flow through pressure letdown valve 57 configured to reduce the pressure of liquid crude methanol stream 85 to produce low pressure crude methanol stream 86. In embodiments of the invention, low pressure crude methanol stream 86 may be at a pressure of 3 to 5 kg/cm² and all ranges and values there between including 3 to 3.2 kg/cm², 3.2 to 3.4 kg/cm², 3.4 to 3.6 kg/cm², 3.6 to 3.8 kg/cm², 3.8 to 4.0 kg/cm², 4.0 to 4.2 kg/cm², 4.2 to 4.4 kg/cm², 4.4 to 4.6 kg/cm², 4.6 to 4.8 kg/cm², and 4.8 to 5.0 kg/cm².

In embodiments of the invention, an outlet of pressure let down valve 57 is in fluid communication with dewaxing unit 101 such that low pressure crude methanol stream 86 flows from pressure let down valve 57 to dewaxing unit 101. According to embodiments of the invention, dewaxing unit 101 is adapted to remove paraffin wax from low pressure crude methanol stream 86 to produce wax-free methanol stream 88. In embodiments of the invention, wax-free methanol stream 88 comprises a negligible amount of paraffin wax.

According to embodiments of the invention, dewaxing unit 101 comprises one or more cooling units arranged in parallel with each other. Dewaxing unit 101 may comprise feed inlet 93 in fluid communication with one or more cooling units. In embodiments of the invention, the fluid communication is controlled by one or more valves between and/or in fluid communication with feed inlet 93 and one or more cooling units. In embodiments of the invention, dewaxing unit 101 comprises first cooling unit 61 and second cooling unit 60 arranged in parallel with each other, as shown in FIG. 1A. First cooling unit 61 and second cooling unit 60 may be configured to remove paraffin wax from low pressure crude methanol stream 86 to produce final unfiltered methanol stream 87. In embodiments of the invention, only one of first cooling unit 61 and second cooling unit 60 is online during normal operation.

According to embodiments of the invention, when first cooling unit 61 is online, both valves 59 and 63 are open and second cooling unit 60 is idle (offline) with valves 58 and 62 both closed. When second cooling unit 60 is online, first cooling unit 61 is idle (offline) with valves 59 and 63 both closed. In embodiments of the invention, paraffinic wax of low pressure crude methanol stream 86 deposits in first cooling unit 61 as low pressure crude methanol stream 86 is cooled. In embodiments of the invention, when performance of first cooling unit 61 deteriorates due to increased wax deposition therein, low pressure crude methanol stream 86 is routed to second cooling unit 60 with valves 58 and 62 open to ensure continuous operation. Meanwhile, first cooling unit 61 is taken offline and cleaned to remove the wax deposit therein using an organic solvent. Exemplary organic solvents may include aromatic solvents (e.g., o-xylene), diesel-range alkanes (e.g., hexadecane), cycloalkanes (e.g., cyclohexane, cyclooctane), and combinations thereof.

In embodiments of the invention, dewaxing unit 101 further includes one or more filters arranged in parallel with each other configured to remove any traces of paraffin wax, if any, from final unfiltered methanol stream 87 to form wax-free methanol stream 88. According to embodiments of the invention, the one or more filters are configured to filter wax in final unfiltered methanol stream 87 when final unfiltered methanol stream 87 contains paraffin wax. In embodiments of the invention, the one or more filters may include first hydrophobic filter 67 and second hydrophobic filter 66 in fluid communication with a filter feed inlet. The fluid communication may be controlled by one or more valves (e.g., valves 65 and 69) between and/or in fluid communication with the filter feed inlet and first hydrophobic filter 67, and/or one or more valves (e.g., valves 64 and 68) between and/or in fluid communication with the filter feed inlet and second hydrophobic filter 66. In embodiments of the invention, first hydrophobic filter 67 and second hydrophobic filter 66 may be arranged in parallel. Only one of first hydrophobic filter 67 and second hydrophobic filter 66 is online and the other is on standby mode. When first hydrophobic filter 67 is online, valves 65 and 69 are both open and second hydrophobic filter 66 is idle (offline) with both valves 64 and 68 closed. When second hydrophobic filter 66 is online, valves 64 and 68 are open and first hydrophobic filter 67 is idle (offline) with both valves 65 and 69 closed.

Figure 2:
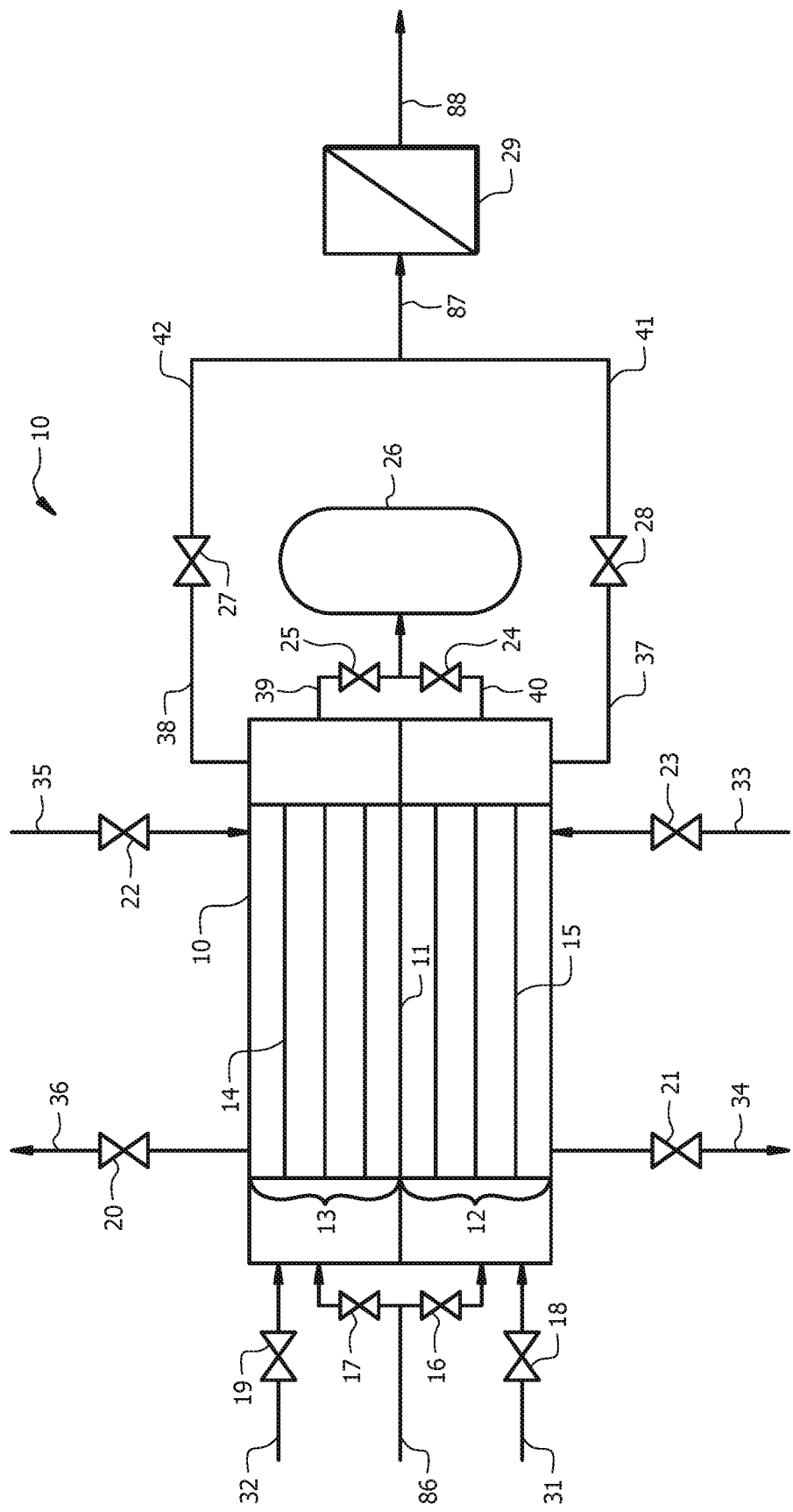
FIG. 2 shows a schematic diagram of a dewax heat exchanger of a dewaxing unit, according to embodiments of the invention.

According to embodiments of the invention, dewaxing unit 101 comprising dewax heat exchanger 10 is shown in FIG. 2. Dewax heat exchanger 10 may be horizontal or vertical. In embodiments of the invention, dewax heat exchanger 10 comprises a shell divided by metal sheet 11 to form first chamber 12 and second chamber 13. Dewax heat exchanger 10 may comprise a plurality of first tube bundles 15 disposed in first chamber 12 and a plurality of second tube bundles 14 disposed in second chamber 13. In embodiments of the invention, first tube bundles 15 may be in fluid communication with second tube bundles 14 through valves 16 and 17. In embodiments of the invention, each of first chamber 12 and second chamber 13 may contain 1, 3, or 5 tube passes. According to embodiments of the invention, dewax heat exchanger 10 is configured to have a residence time sufficient to condense substantially all paraffin wax in low pressure crude methanol stream 86 in tubes of first chamber 12 and/or second chamber 13. In embodiments of the invention, each of first chamber 12 and second chamber 13 has an independent inlet and outlet for condensing medium, low pressure crude methanol stream 86, and cleaning fluid streams.

In embodiments of the invention, dewax heat exchanger 10 comprises first cleaning fluid inlet valve 18 adapted to control first cleaning fluid stream 31 flowing into first chamber 12. In embodiments of the invention, dewax heat exchanger 10 comprises second cleaning fluid inlet valve 19 adapted to control second cleaning fluid stream 32 flowing into second chamber 13. According to embodiments of the invention, dewax heat exchanger 10 comprises first condensing medium inlet valve 23 adapted to control first condensing medium inlet stream 33 flowing into first chamber 12. Dewax heat exchanger 10 may further comprise first condensing medium outlet valve 21 adapted to control first condensing medium outlet stream 34 exiting first chamber 12. In embodiments of the invention, dewax heat exchanger 10 comprises second condensing medium inlet valve 22 adapted to control second condensing medium inlet stream 35 flowing into second chamber 13. Dewax heat exchanger 10 may further comprise second condensing medium outlet valve 20 adapted to control second condensing medium outlet stream 36 exiting second chamber 13.

In embodiments of the invention, low pressure crude methanol stream 86 may be routed to tubes of first tube bundle 15 via valve 16 and/or tubes of second tube bundle 14 via valve 17. Dewax heat exchanger 10 may be adapted to rout condensing medium to first chamber 12 and/or second chamber 13 via first condensing medium inlet valve 23 and second condensing medium inlet valve 22, respectively. The cleaning fluid stream can be fed to the tubes via first cleaning fluid inlet valve 18 and second cleaning fluid inlet valve 19 during cleaning process of tubes in first chamber 12 and/or second chamber 13. Exemplary condensing medium may include water. Exemplary cleaning fluid may include aromatic solvents (e.g., o-xylene), diesel-range alkanes (e.g., hexadecane), cycloalkanes (e.g., cyclohexane, cyclooctane), and combinations thereof. First unfiltered methanol stream 37 can be routed from first tube bundles 15. Second unfiltered methanol stream 38 can be routed from second tube bundles 14. First unfiltered methanol stream 37 flows through valve 28 to form stream 41. Second unfiltered methanol stream 38 flows through valve 27 to form stream 42. Stream 41 and/or stream 42 then form final unfiltered methanol stream 87. Dewax heat exchanger 10 may further comprise filter unit 29 configured to filter wax in final unfiltered methanol stream 87, when final unfiltered methanol stream 87 contains paraffin wax, to form wax-free methanol stream 88. Filter unit 29 may include two filters in parallel. In embodiments of the invention, only one filter of filter unit 29 is online when dewax heat exchanger 10 is in operation.

In embodiments of the invention, dewax heat exchanger 10 may include wax collection tank 26 in fluid communication with an outlet of first chamber 12 such that first wax containing cleaning fluid stream 40 flows from first chamber 12 to wax collection tank 26. Wax collection tank 26 may be in fluid communication with an outlet of second chamber 13 such that second wax containing cleaning fluid stream 39 flows from second chamber 13 to wax collection tank 26. Flow of first wax containing cleaning fluid stream 40 may be controlled by valve 24. Flow of second wax containing cleaning fluid stream 39 may be controlled by valve 25. Wax collection tank 26 may be adapted to collect cleaning fluid and/or paraffin wax.

According to embodiments of the invention, first chamber 12 and second chamber 13 of dewax heat exchanger 10 can be operated independently. First chamber 12 and second chamber 13 of dewax heat exchanger 10 as shown in FIG. 2 can be operated as equivalents to first cooling unit 61 and second cooling unit 60 of dewaxing unit 101 shown in FIGS. 1A and 1B, respectively. In embodiments of the invention, when low pressure crude methanol stream 86 is routed to second chamber 13, valve 17, second condensing medium outlet valve 20, second condensing medium inlet valve 22, and valve 27 are open, and second cleaning fluid inlet valve 19, valve 25, valve 16, valve 28, first condensing medium inlet valve 23, and first condensing medium outlet valve 21 are closed. In embodiments of the invention, as soon as second chamber 13 is saturated with wax, low pressure crude methanol stream 86 is routed to first chamber 12 while second chamber 13 is switched to cleaning mode before it is ready for the next cycle.

According to embodiments of the invention, when low pressure crude methanol stream 86 is routed to first chamber 12, valve 16, first condensing medium outlet valve 21, first condensing medium inlet valve 23, and valve 28 are open while first cleaning fluid inlet valve 18, valve 24, valve 17, valve 27, second condensing medium inlet valve 22, and second condensing medium outlet valve 20 are closed. During cleaning stage of first chamber 12 or second chamber 13, the cleaning fluid inlet and cleaning fluid outlet valves for the chamber being cleaned can be opened while low pressure crude methanol stream 86 is processed in the other chamber. For instance, while low pressure crude methanol stream 86 is being processed in first chamber 12, second cleaning fluid inlet valve 19 and valve 25 for second chamber 13 can be opened during the cleaning process. When low pressure crude methanol stream 86 is being processed in second chamber 13, first cleaning fluid inlet valve 18 and valve 24 for first chamber 12 can be opened during the cleaning process.

According to embodiments of the invention, as shown in FIG. 1A, a second outlet of first vapor-liquid separator 53 may be in fluid communication with gas cooler 54 such that first vapor stream 80 flows from first vapor-liquid separator 53 to gas cooler 54. Gas cooler 54 may be adapted to cool first vapor stream 80 to produce cooled stream 81. In embodiments of the invention, gas cooler 54 may use water as a cooling medium. Cooled stream 81 may be at a temperature of 30 to 50° C. and all ranges and values there between including ranges of 30 to 32° C., 32 to 34° C., 34 to 36° C., 36 to 38° C., 38 to 40° C., 40 to 42° C., 42 to 44° C., 44 to 46° C., 46 to 48° C., and 48 to 50° C. Cooled stream 81 may include methanol in liquid phase, and unreacted carbon monoxide, hydrogen, carbon dioxide, nitrogen, and methane in gas phase. In embodiments of the invention, an outlet of gas cooler 54 may be in fluid communication with an inlet of second vapor-liquid separator 55 such that cooled stream 81 flows from gas cooler 54 to second vapor-liquid separator 55.

In embodiments of the invention, second vapor-liquid separator 55 is a low-temperature vapor-liquid separator. Second vapor-liquid separator 55 is adapted to separate cooled stream 81 to produce recycle gas stream 82 comprising primarily hydrogen, carbon dioxide, nitrogen, and carbon monoxide, and additional methanol stream 84 comprising primarily methanol. Additional methanol stream 84 may comprise substantially no paraffin wax. In embodiments of the invention, a portion of recycle gas stream 82 may be purged as purge stream 91 and the remainder of recycle gas stream 82 forms remainder recycle stream 83. An outlet of second vapor-liquid separator 55 may be in fluid communication with recycle compressor 56 such that remainder recycle stream 83 flows to recycle compressor 56. Recycle compressor 56 may be adapted to compress remainder recycle stream 83. Compressed remainder recycle stream 83 may be combined with make-up syngas stream 74 to form feed stream 75 for methanol synthesis unit 50. In embodiments of the invention, purging of recycle gas stream 82 as purge stream 91 is configured to avoid accumulation of inert gas (nitrogen and methane) components in the heated feed stream 76.

According to embodiments of the invention, an outlet of dewaxing unit 101 may be in fluid communication with an inlet of letdown tank 70 such that wax-free methanol stream 88 flows from dewaxing unit 101 to letdown tank 70. An outlet of second vapor-liquid separator 55 may be in fluid communication with an inlet of letdown tank 70 via a pressure letdown valve (not shown) such additional methanol stream 84 flows from second vapor-liquid separator 55 to letdown tank 70. In embodiments of the invention, wax-free methanol stream 88 and additional methanol stream 84 are combined to form combined methanol stream 92. Combined methanol stream 92 flows to letdown tank 70. In embodiments of the invention, an outlet of letdown tank 70 may be in fluid communication with a conventional separation unit such that dewaxed product stream 89 flows from letdown tank 70 to the conventional separation unit. In embodiments of the invention, dewaxed product stream 89 has substantially the same composition as combined methanol stream 92. The conventional separation unit may be configured to separate water and/or dissolved gases from methanol. In embodiments of the invention, the conventional separation unit may include scrubbing and distillation units.

Figure 1B:
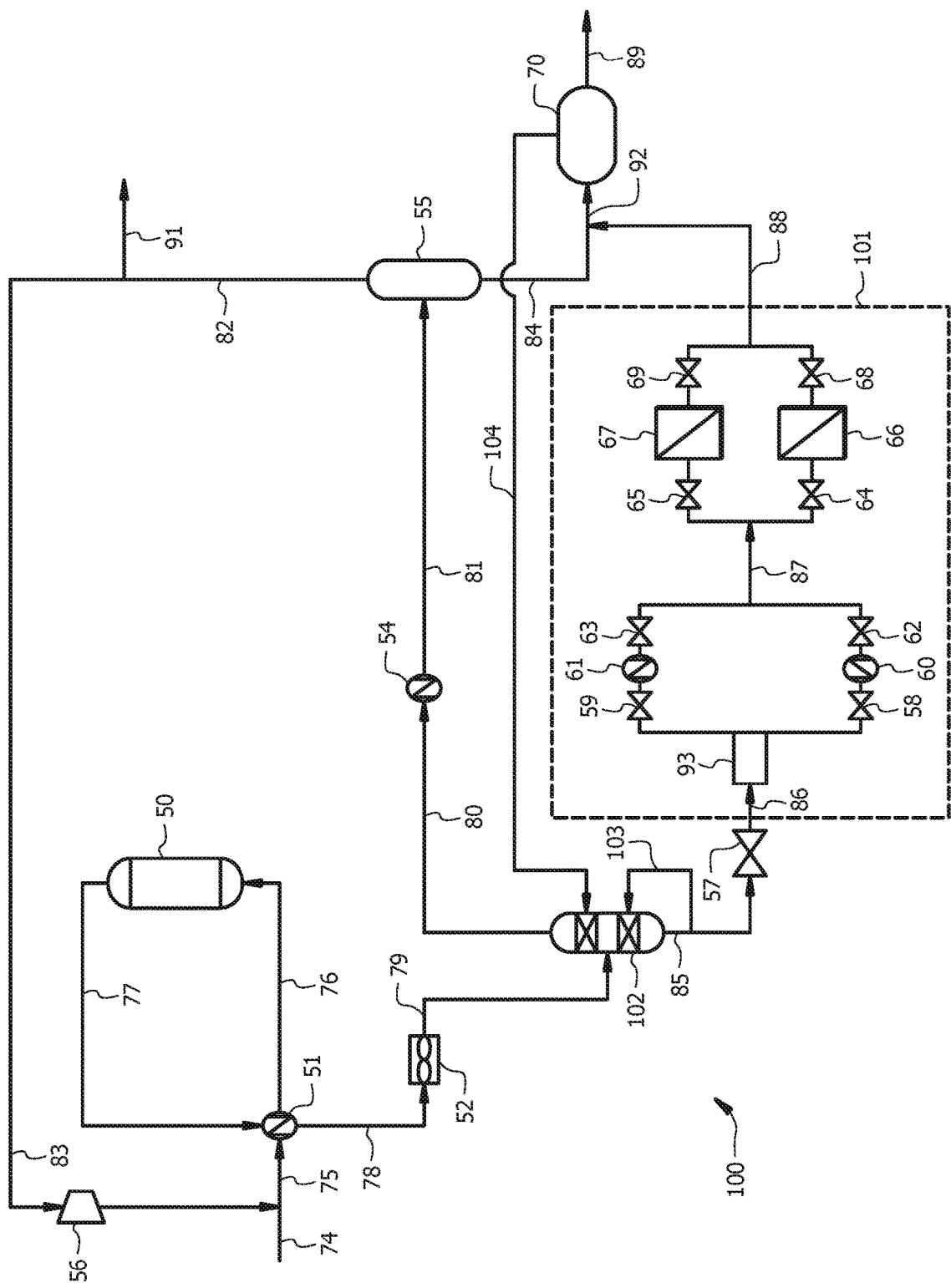
FIG. 1B shows a schematic diagram of a system for producing methanol that includes a methanol wash column for separating an effluent stream of the methanol synthesis unit, according to embodiments of the invention.

According to embodiments of the invention, as shown in FIG. 1B, first vapor-liquid separator 53 of system 100 can be replaced by wash column 102 configured to separate second cooled product stream 79 into first vapor stream 80 and liquid crude methanol stream 85 via washing. In embodiments of the invention, wash medium used in the wash column may include methanol. The methanol used as the wash medium in wash column 102 may be from letdown tank 70 via first wash medium stream 104 and/or a portion of liquid crude methanol stream 85 via recycle crude methanol stream 103. In embodiments of the invention, about 15-60% of methanol from letdown tank 70 may be recycled to wash column 102 as wash medium.

B. Methods for Producing and Processing Crude Methanol

Figure 3:
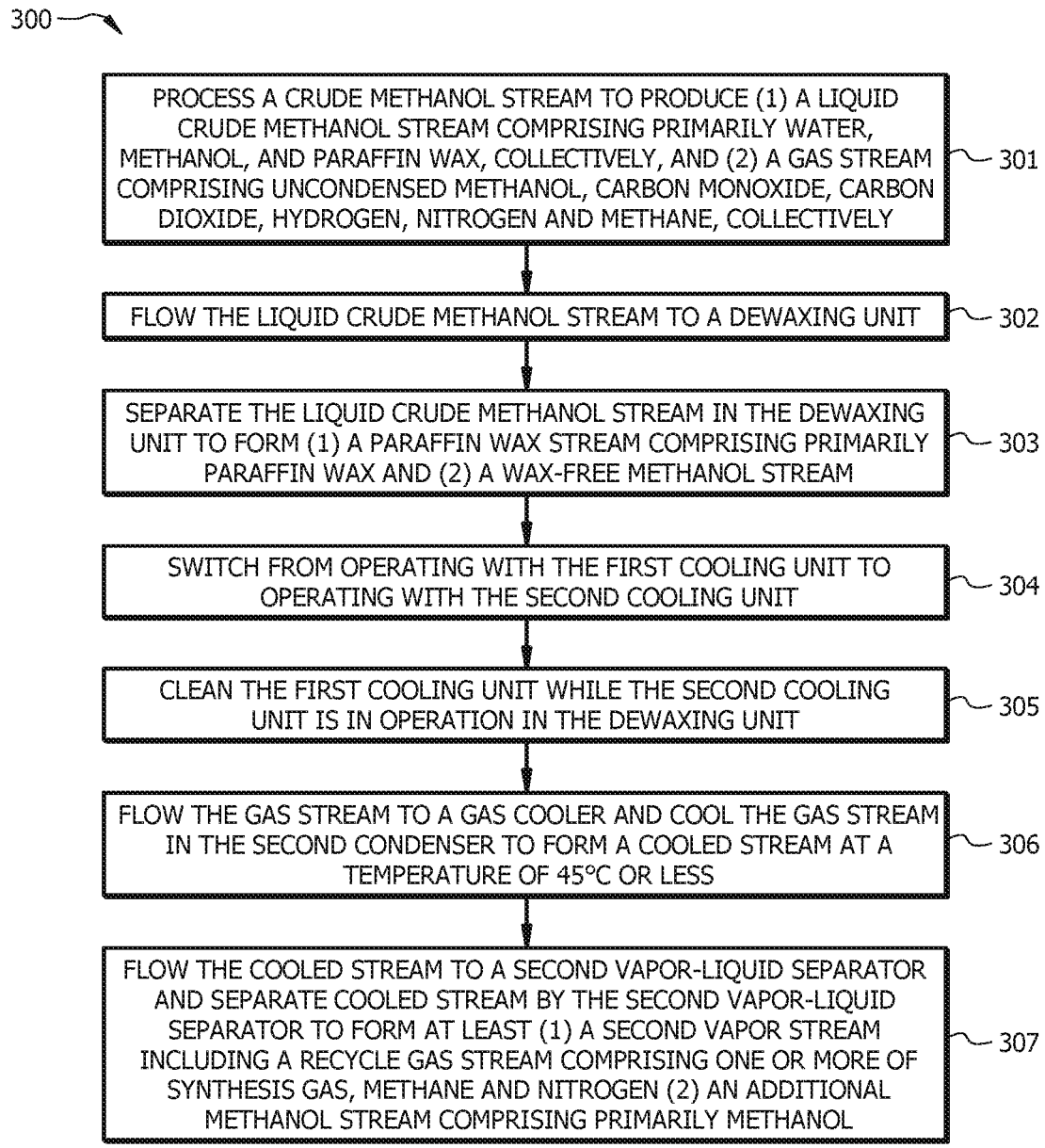
FIG. 3 shows a schematic flowchart for a method of processing crude methanol, according to embodiments of the invention.

Methods of processing crude methanol produced using carbon monoxide, carbon dioxide, and hydrogen have been discovered. The method may be capable of avoiding loss of production time caused by cleaning the dewaxing unit of the methanol production system. As shown in FIG. 3, embodiments of the invention include method 300 for producing and processing crude methanol. Method 300 may be implemented by system 100 and/or dewax heat exchanger 10, as shown in FIGS. 1A, 1B and 2. According to embodiments of the invention, as shown in block 301, method 300 comprises processing a crude methanol stream, which may include product stream 77, to produce liquid crude methanol stream 85 comprising primarily water, methanol, and paraffin wax, collectively.

In embodiments of the invention, processing at block 301 may include flowing product stream 77 comprising paraffin wax to feed effluent heat exchanger 51, and cooling product stream 77, by feed effluent heat exchanger 51, to form a cooled crude methanol stream (e.g., first cooled product stream 78). In embodiments of the invention, the paraffin wax includes $C_{18}$ paraffin ($C_{18}H_{38}$) to $C_{60}$ paraffin ($C_{60}H_{122}$). The cooled crude methanol stream may be at a temperature in a range of 120 to 135° C. and all ranges and values there between include ranges of 120 to 121° C., 121 to 122° C., 122 to 123° C., 123 to 124° C., 124 to 125° C., 125 to 126° C., 126 to 127° C., 127 to 128° C., 128 to 129° C., 129 to 130° C., 130 to 131° C., 131 to 132° C., 132 to 133° C., 133 to 134° C., and 134 to 135° C. The cooled crude methanol stream may comprise about 94 to 98 vol. % vapor. Processing at block 301 may further include flowing first cooled product stream 78 into cooler 52 or a first condenser and cooling first cooled product stream 78 stream in cooler 52 or the first condenser to form a partially condensed stream, which may be second cooled product stream 79. The partially condensed stream may be at a temperature of 72 to 80° C. and all ranges and values there between including 73° C., 74° C., 75° C., 76° C., 77° C., 78° C., and 79° C. The partially condensed stream may comprise 86 to 90 vol. % vapor. Processing at block 301 may further still include flowing the partially condensed stream to a first separator that may include first vapor-liquid separator 53 or wash column 102, and separating the partially condensed stream by the first separator to form at least (1) first vapor stream 80 comprising one or more of hydrogen, carbon monoxide, carbon dioxide, methane, water and nitrogen, and (2) liquid crude methanol stream 85 comprising primarily water, methanol and paraffin, wax, collectively. Liquid crude methanol stream 85 may comprise 65 to 75% of the methanol from product stream 77 and all ranges and values there between including 66%, 67%, 68%, 69%, 70%, 71%, 72%, 73%, and 74%.

According to embodiments of the invention, as shown in block 302, method 300 includes flowing liquid crude methanol stream 85 to dewaxing unit 101. As shown in block 303, method 300 may further comprise separating liquid crude methanol stream 85, in dewaxing unit 101, to form (1) a paraffin wax stream comprising primarily paraffin wax and (2) wax-free methanol stream 88. In embodiments of the invention, dewaxing unit 101 may be operated such that while first cooling unit 61 is online carrying out the separating of liquid crude methanol stream, second cooling unit 60 is offline, or vice versa. In embodiments of the invention, dewaxing unit 101 may use air and/or water as cooling medium. Dewaxing unit 101 may cool liquid crude methanol stream 85 to a temperature of 30 to 50° C. and all ranges and values there between including ranges of 30 to 31° C., 31 to 32° C., 32 to 33° C., 33 to 34° C., 34 to 35° C., 35 to 36° C., 36 to 37° C., 37 to 38° C., 38 to 39° C., 39 to 40° C., 40 to 41° C., 41 to 42° C., 42 to 43° C., 43 to 44° C., 44 to 45° C., 45 to 46° C., 46 to 47° C., 47 to 48° C., 48 to 49° C., and 49 to 50° C. Dewaxing unit 101 may be operated at a liquid pressure of 2 to 6 kg/cm$^2$ and all ranges and values there between including ranges of 2 to 2.5 kg/cm$^2$, 2.5 to 3 kg/cm$^2$, 3 to 3.5 kg/cm$^2$, 3.5 to 4 kg/cm$^2$, 4 to 4.5 kg/cm$^2$, and 4.5 to 5 kg/cm$^2$, 5 to 5.5 kg/cm$^2$, and 5.5 to 6 kg/cm$^2$. Wax-free methanol stream 88 may comprise negligible or less than 2 ppm paraffin wax by weight.

According to embodiments of the invention, as shown in block 304, method 300 further includes switching from operating with first cooling unit 61 to operating with second cooling unit 60. The operating may include performing the function of cooling low pressure crude methanol stream 86 to remove paraffin wax therefrom. In embodiments of the invention, the switching at block 304 include controlling valves 58, 59, 62 and 63 to ensure low pressure crude methanol stream 86 flows through second cooling unit 60 and not through first cooling unit 61. According to embodiments of the invention, as shown in block 305, method 300 further includes cleaning first cooling unit 61 while second cooling unit 60 is in operation in dewaxing unit 101. In embodiments of the invention, cleaning at block 305 may include using a cleaning medium, comprising aromatic solvents (e.g., o-xylene), diesel-range alkanes (e.g., hexadecane), cycloalkanes (e.g., cyclohexane, cyclooctane), or combinations thereof, to remove paraffin wax deposit in first cooling unit 61.

According to embodiments of the invention, as shown in block 306, method 300 further comprises flowing first vapor stream 80 to gas cooler 54 (or a second condenser) and cooling first vapor stream 80, in gas cooler 54 (or the second condenser), to form cooled stream 81 at a temperature of 45° C. or less. In embodiments of the invention, as shown in block 307, method 300 further comprises flowing cooled stream 81 to second vapor-liquid separator 55 and separating cooled stream by second vapor-liquid separator 55 to form at least (1) a second vapor stream including recycle gas stream 82, comprising one or more of synthesis gas and methane and (2) additional methanol stream 84 comprising primarily methanol. In embodiments of the invention, additional methanol stream 84 and wax-free methanol stream 88 is flowed to letdown tank 70.

Although embodiments of the present invention have been described with reference to blocks of FIG. 3, it should be appreciated that operation of the present invention is not limited to the particular blocks and/or the particular order of the blocks illustrated in FIG. 3. Accordingly, embodiments of the invention may provide functionality as described herein using various blocks in a sequence different than that of FIG. 3.

In the context of the present invention, at least the following 15 embodiments are disclosed. Embodiment 1 is a method of processing crude methanol that contains paraffin wax. The method includes processing a crude methanol stream to produce a first liquid stream containing primarily water, methanol, and paraffin wax, collectively. The method further includes flowing the first liquid stream to a dewaxing unit, where the dewaxing unit includes a feed inlet, and a first cooling unit and a second cooling unit arranged in parallel with each other, wherein the dewaxing unit is adapted such that the dewaxing unit feed inlet is in fluid communication with the first cooling unit, or the second cooling unit, or both, wherein the fluid communication is controlled by one or more valves between and/or in fluid communication with the dewaxing unit feed inlet and the first cooling unit, and/or one or more valves between and/or in fluid communication with the dewaxing unit feed inlet and the second cooling unit. In addition, the method includes separating the first liquid stream, in the dewaxing unit, to form (1) a paraffin wax stream containing primarily paraffin wax and (2) a dewaxed crude methanol stream. Embodiment 2 is the method of embodiment 1, wherein the dewaxing unit further includes a filter feed inlet, and a first hydrophobic filter and a second hydrophobic filter arranged in parallel with each other, wherein the dewaxing unit is adapted such that the filter feed inlet is in fluid communication with the first hydrophobic filter, or the second hydrophobic filter, or both, wherein the fluid communication is controlled by one or more valves between and/or in fluid communication with the filter feed inlet and the first hydrophobic filter and/or one or more valves between and/or in fluid communication with the filter feed inlet and the second hydrophobic filter. Embodiment 3 is the method of either of embodiments 1 or 2, further including switching from operating with the first cooling unit to operating with the second cooling unit, and cleaning the first cooling unit while the second cooling unit is in operation in the dewaxing unit. Embodiment 4 is the method of any of embodiments 1 to 3, wherein the methanol in the first liquid stream includes about 65 to 75% of the methanol from the crude methanol stream. Embodiment 5 is the method of any of embodiments 1 to 4, wherein the step of processing the crude methanol stream includes flowing a crude methanol stream comprising paraffin wax to a heat exchanger, and cooling the crude methanol stream, by the heat exchanger, to form a cooled crude methanol stream. The method further includes flowing the cooled crude methanol stream to a first condenser, and cooling the cooled crude methanol stream, in the first condenser, to form a partially condensed stream. In addition, the method includes flowing the partially condensed stream to a first separator, and separating the partially condensed stream, by the first separator, to form at least (1) a first vapor stream containing one or more of hydrogen, carbon monoxide, carbon dioxide, methane, water and nitrogen; and (2) the first liquid stream containing primarily water, methanol, and paraffin wax, collectively. Embodiment 6 is the method of embodiment 5, wherein the first separator includes a vapor-liquid separator and/or a wash column. Embodiment 7 is the method of embodiment 6, wherein the wash column is operated using a wash medium comprising a portion of dewaxed crude methanol stream and/or a portion of the first liquid stream. Embodiment 8 is the method of any of embodiments 5 to 7, further including flowing the first vapor stream to a second condenser, and cooling the first vapor stream, in the second condenser, to form a cooled first vapor stream at a temperature of 45° C. or less. The method further includes flowing the cooled first vapor stream to a second separator, and separating the cooled first vapor stream, by the second separator, to form at least (1) a second vapor stream comprising one or more of synthesis gas and methane and (2) a second liquid stream comprising primarily methanol. Embodiment 9 is the method of embodiment 8, wherein the methanol in the second liquid stream includes 8 to 18% of the methanol in the crude methanol stream. Embodiment 10 is the method of any of embodiments 5 to 9, wherein the cooled crude methanol stream is at a temperature in a range of 120 to 135° C. Embodiment 11 is the method of any of embodiments 5 to 10, wherein the cooled crude methanol stream contains 94 to 98 vol. % vapor. Embodiment 12 is the method of any of embodiments 5 to 11, wherein the partially condensed stream is at a temperature of 72 to 80° C. Embodiment 13 is the method of any of embodiments 5 to 12, wherein the partially condensed stream contains 86 to 90 vol. % vapor. Embodiment 14 is the method of any of embodiments 1 to 13, wherein the dewaxing unit is operated at a liquid pressure of 2 to 6 kg/cm²g. Embodiment 15 is the method of any of embodiments 1 to 14, wherein the dewaxing unit uses a cooling medium comprising air and/or water.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of processing crude methanol that comprises paraffin wax, the method comprising:
    processing a crude methanol stream to produce a first liquid stream comprising primarily water, methanol, and paraffin wax, collectively;
    flowing the first liquid stream to a dewaxing unit, the dewaxing unit comprising:
    a feed inlet;
    a first cooling unit and a second cooling unit arranged in parallel with each other;
    a filter feed inlet; and
    a first hydrophobic filter and a second hydrophobic filter arranged in parallel with each other;
    wherein the dewaxing unit is adapted such that the feed inlet of the dewaxing unit is in fluid communication with the first cooling unit, or the second cooling unit, or both, wherein the fluid communication is controlled by one or more valves between and/or in fluid communication with the feed inlet of the dewaxing unit and the first cooling unit, and/or one or more valves between and/or in fluid communication with the feed inlet of the dewaxing unit and the second cooling unit;
    wherein the dewaxing unit is adapted such that the filter feed inlet is in fluid communication with the first hydrophobic filter, or the second hydrophobic filter, or both, wherein the fluid communication is controlled by one or more valves between and/or in fluid communication with the filter feed inlet and the first hydrophobic filter, and/or one or more valves between and/or in fluid communication with the filter feed inlet and the second hydrophobic filter;
    wherein the filter feed inlet receiving an unfiltered methanol stream from the first cooling unit and/or the second cooling unit; and
    separating the unfiltered methanol stream to form (1) a paraffin wax stream comprising primarily paraffin wax and (2) a dewaxed crude methanol stream.

2. The method of claim 1, further comprising:
    switching from operating with the first cooling unit to operating with the second cooling unit; and
    cleaning the first cooling unit while the second cooling unit is in operation in the dewaxing unit.

3. The method of claim 1, wherein the methanol in the first liquid stream includes about 65 to 75% of the methanol from the crude methanol stream.

4. The method of claim 1, wherein the step of processing the crude methanol stream to produce the first liquid stream comprises:
    flowing a crude methanol stream comprising paraffin wax to a heat exchanger;
    cooling the crude methanol stream, by the heat exchanger, to form a cooled crude methanol stream;
    flowing the cooled crude methanol stream to a first condenser;
    cooling the cooled crude methanol stream, in the first condenser, to form a partially condensed stream;

flowing the partially condensed stream to a first separator; and separating the partially condensed stream, by the first separator, to form at least (1) a first vapor stream comprising one or more of hydrogen, carbon monoxide, carbon dioxide, methane, nitrogen, uncondensed methanol, and water; and (2) the first liquid stream comprising primarily water, methanol, and paraffin wax, collectively.

5. The method of claim 4, wherein the first separator comprises a vapor-liquid separator and/or a wash column.

6. The method of claim 5, wherein the wash column is operated using a wash medium comprising a portion of dewaxed crude methanol stream and/or a portion of the first liquid stream.

7. The method of claim 4, further comprising:
flowing the first vapor stream to a second condenser;
cooling the first vapor stream, in the second condenser, to form a cooled first vapor stream at a temperature of 45° C. or less;
flowing the cooled first vapor stream to a second separator; and
separating the cooled first vapor stream, by the second separator, to form at least (1) a second vapor stream comprising one or more of synthesis gas and methane and (2) a second liquid stream comprising primarily methanol.

8. The method of claim 7, wherein the methanol in the second liquid stream includes 8 to 18% of the methanol in the crude methanol stream.

9. The method of claim 4, wherein the cooled crude methanol stream is at a temperature in a range of 120 to 135° C.

10. The method of claim 4, wherein the cooled crude methanol stream comprises 94 to 98 vol. % vapor.

11. The method of claim 4, wherein the partially condensed stream is at a temperature of 72 to 80° C.

12. The method of claim 4, wherein the partially condensed stream comprises 86 to 90 vol. % vapor.

13. The method of claim 1, wherein the dewaxing unit uses a cooling medium comprising air and/or water.

14. A method of processing crude methanol that comprises paraffin wax, the method comprising:
processing a crude methanol stream to produce a first liquid stream comprising primarily water, methanol, and paraffin wax, collectively;
flowing the first liquid stream to a dewaxing unit, the dewaxing unit comprising:
a feed inlet; and
a first cooling unit and a second cooling unit arranged in parallel with each other, wherein the dewaxing unit is adapted such that the feed inlet of the dewaxing unit is in fluid communication with the first cooling unit, or the second cooling unit, or both, wherein the fluid communication is controlled by one or more valves between and/or in fluid communication with the feed inlet of the dewaxing unit and the first cooling unit, and/or one or more valves between and/or in fluid communication with the feed inlet of the dewaxing unit and the second cooling unit; and
separating the first liquid stream, in the dewaxing unit, to form (1) a paraffin wax stream comprising primarily paraffin wax and (2) a dewaxed crude methanol stream, wherein the dewaxing unit is operated at a liquid pressure of 2 to 6 $kg/cm^2g$.

15. The method of claim 1, wherein the dewaxing unit is operated at a liquid pressure of 2 to 6 $kg/cm^2g$.

16. The method of claim 2, wherein the dewaxing unit is operated at a liquid pressure of 2 to 6 $kg/cm^2g$.

17. The method of claim 3, wherein the dewaxing unit is operated at a liquid pressure of 2 to 6 $kg/cm^2$ g.

18. The method of claim 4, wherein the dewaxing unit is operated at a liquid pressure of 2 to 6 $kg/cm^2g$.

19. The method of claim 5, wherein the dewaxing unit is operated at a liquid pressure of 2 to 6 $kg/cm^2g$.

20. The method of claim 4, wherein the first separator comprises a vapor-liquid separator.

21. The method of claim 4, wherein the first separator comprises a wash column.

* * * * *